United States Patent
Pini et al.

(10) Patent No.: US 11,104,705 B2
(45) Date of Patent: Aug. 31, 2021

(54) METHODS FOR REMOVING BACTERIAL TOXINS FROM A BIOLOGICAL FLUID

(71) Applicant: SETLANCE S.R.L., Siena (IT)

(72) Inventors: Alessandro Pini, Siena (IT); Chiara Falciani, Siena (IT); Luisa Bracci, Siena (IT); Jlenia Brunetti, Siena (IT); Leila Quercini, Siena (IT)

(73) Assignee: SETLANCE S.R.L., Siena (IT)

( * ) Notice: Subject to any disclaimer, the term of this patent is extended or adjusted under 35 U.S.C. 154(b) by 0 days.

(21) Appl. No.: 16/605,898

(22) PCT Filed: Apr. 19, 2018

(86) PCT No.: PCT/EP2018/059979
§ 371 (c)(1),
(2) Date: Oct. 17, 2019

(87) PCT Pub. No.: WO2018/193011
PCT Pub. Date: Oct. 25, 2018

(65) Prior Publication Data
US 2020/0048307 A1 Feb. 13, 2020

(30) Foreign Application Priority Data
Apr. 20, 2017 (EP) .................................. 17167353

(51) Int. Cl.
| A61K 38/00 | (2006.01) |
| A61K 38/08 | (2019.01) |
| C07K 7/06 | (2006.01) |
| C07K 17/08 | (2006.01) |
| C07K 17/10 | (2006.01) |
| C07K 14/47 | (2006.01) |

(52) U.S. Cl.
CPC ............ *C07K 7/06* (2013.01); *C07K 14/4723* (2013.01); *C07K 17/08* (2013.01); *C07K 17/10* (2013.01); *A61K 38/00* (2013.01)

(58) Field of Classification Search
CPC .... A61K 38/00; A61K 38/08; C07K 14/4723; C07K 7/06; C07K 7/10; C07K 7/08

USPC .................................. 530/300, 328; 514/2.4
See application file for complete search history.

(56) References Cited

U.S. PATENT DOCUMENTS 8,440,794 B2 * 5/2013 Bracci ..................... A61P 31/04
530/328

FOREIGN PATENT DOCUMENTS

| EP | 1232754 A2 | 8/2002 |
| EP | 1789436 A1 | 5/2007 |
| WO | 1999006440 A1 | 2/1999 |
| WO | 2010038220 A1 | 4/2010 |
| WO | 2012010266 A1 | 1/2012 |

OTHER PUBLICATIONS

Costa F. et al, "Covalent immobilization of antimicrobial peptides (AMPs) onto biomaterial surfaces", Acta Biomaterialia, vol. 7, No. 4, Nov. 1, 2010, pp. 1431-1440.
Falciani C. et al., "Isomerization of an antimicrobial peptide broadens antimicrobial spectrum to gram-positive bacterial pathogens", PLOS ONE, vol. 7, No. 10, Oct. 2, 2012, p. e46259.
Gustafsson A. et al., "LPS interactions with immobilized and soluble antimicrobial peptides" Scandinavian Journal of Clinical & Laboratory Investigation, vol. 70, No. 3, Jan. 19, 2010, pp. 194-200.
Search Report and Written Opinion of PCT/EP2018/059979 dated Jul. 19, 2018.

* cited by examiner

*Primary Examiner* — Julie Ha
(74) *Attorney, Agent, or Firm* — Silvia Salvadori, P.C.; Silvia Salvadori

(57) ABSTRACT

Methods for removing bacterial toxins such as lipopolysaccharide and lipoteichoic acid from a biological fluid with a peptide selected from KKIRVRLSA (SEQ ID NO:1), RRIRVRLSA (SEQ ID NO:2), KRIRVRLSA (SEQ ID NO:3) and RKIRVRLSA (SEQ ID NO:4), the peptide being covalently attached to a solid support through the C-terminus, optionally with the interposition of a linker.

10 Claims, 7 Drawing Sheets
Specification includes a Sequence Listing.

A

B

METHODS FOR REMOVING BACTERIAL TOXINS FROM A BIOLOGICAL FLUID

This application is a U.S. national stage of PCT/ep2018/059979 filed on 19 Apr. 2018, which claims priority to and the benefit of European Application No. 17167353.6 filed on 20 Apr. 2017, the contents of which are incorporated herein by reference in their entireties.

This invention relates to methods for removing bacterial toxins such as lipopolysaccharide and lipoteichoic acid from a biological fluid. In such method a peptide, selected from the list of KKIRVRLSA (SEQ ID NO:1), RRIRVRLSA (SEQ ID NO:2), KRIRVRLSA (SEQ ID NO:3) and RKIRVRLSA (SEQ ID NO:4), is covalently attached to a solid support through its C-terminus, optionally with the interposition of a linker, and is used to capture the toxins.

This invention also relates to such derivatised solid supports and to cartridges, columns, and medical apparatuses comprising such derivatised solid supports.

BACKGROUND OF THE INVENTION

Sepsis is a clinical syndrome caused by the body's immune and coagulation systems. Septic shock is a life-threatening condition that is characterized by low blood pressure despite adequate fluid replacement, and organ dysfunction or failure. Sepsis is an important cause of death in people of all ages (Pemer et al, 2017).

For more than two decades, sepsis was defined as a microbial infection that produces fever (or hypothermia), tachycardia, tachypnoea and blood leukocyte changes. Sepsis is now increasingly being considered a deregulated systemic inflammatory and immune response to microbial invasion that produces organ injury. Septic shock is defined as sepsis with hyperlactataemia and concurrent hypotension requiring vasopressor therapy, with in-hospital mortality rates approaching 30-50%.

Sepsis and related disorders are among the leading causes of death throughout the world accounting for 19 million cases each year and 1,400 deaths each day. In a developed country like United States alone, the incidence of sepsis is estimated to be 1,655,000 resulting in more than 250,000 deaths each year. This has become a major economic burden to United States that accounts for a total of $16.7 billion towards healthcare (Lakshmikanth et al, 2016).

Patients suffering from sepsis are usually treated with intravenous antibiotics, oxygen, fluids and drugs to stimulate the heart and to maintain an acceptable blood pressure level. In some cases, dialysis is used.

No specific medical treatment for sepsis has been found, although intensive research is being carried out within this field. With earlier recognition and more compliance to best practices, sepsis has become less of an immediate life-threatening disorder and more of a long-term chronic critical illness, often associated with prolonged inflammation, immune suppression, organ injury and lean tissue wasting. Furthermore, patients who survive sepsis have continuing risk of mortality after discharge, as well as long-term cognitive and functional deficits. Earlier recognition and improved implementation of best practices have reduced in-hospital mortality, but results from the use of immuno-modulatory agents to date have been disappointing. Similarly, no biomarker can definitely diagnose sepsis or predict its clinical outcome. Because of its complexity, improvements in sepsis outcomes are likely to continue to be slow and incremental (Hotchkiss et al, 2016).

Lipopolysaccharide (LPS) or endotoxin, the major constituent of the outer membrane of Gram negative bacteria, is the major bacterial product responsible for the clinical syndrome of sepsis. LPS binding to the host receptor Toll-like receptor 4 (TLR4) triggers an inflammatory reaction characterized by the release of large number of inflammatory mediators that allow the host to respond to the invading pathogen. When this production becomes un-controlled and excessive, it leads to the development of septic shock (Ianaro et al, 2009).

Also the lipoteichoic acid (LTA), a major cell wall component of Gram-positive bacteria, is associated with various inflammatory diseases ranging from minor skin diseases to severe sepsis. It is known that LTA is recognized by Toll-like receptor 2 (TLR2), leading to the initiation of innate immune responses and further development of adaptive immunity. However, excessive immune responses may result in the inflammatory sequelae that are involved in severe diseases such as sepsis (Kang et al, 2016).

TORAYMYXIN (Rocco and Klein 2014; Shoji et al, 1998) is a therapeutic strategy whereby polymyxin B (PMX), a typical antimicrobial peptide already used in clinic (Roscia et al, 2013), is immobilized to a polystyrene-derived fiber in a hemoperfusion device that is used to remove circulating LPS. The PMX cartridge was created by covalently immobilizing PMX to polystyrene-derived fibers, which can then be used to filter blood externally using an extracorporeal circuit, thereby removing circulating LPS through its adsorption to the PMX cartridge.

In a different strategy Polymyxin B (PMX) was immobilized on a solid phase (Sepharose® 4B), and a system of plasmapheresis was developed in the conscious rat, with specific on-line plasma adsorption of endotoxin by a PMX-Sepharose column (Cohen et al, 1987).

The Alteco® LPS Adsorber (Ala-Kokko et al, 2011) is a medical device for extracorporeal removal of LPS during hemoperfusion. The biotechnology of the product is based on a synthetic tailor-made peptide that selectively binds LPS found in the circulation of a septic patient.

There is however a need for alternative methods to deplete blood from LPS, and possibly also from TLA, in septic patients.

PRIOR ART

WO2010038220 discloses the antibacterial peptide sequence KKIRVRLSA (SEQ ID NO:1) (M33) and its functional analogues, RRIRVRLSA (SEQ ID NO:2), KRIRVRLSA (SEQ ID NO:3) and RKIRVRLSA (SEQ ID NO:4) provided in monomeric, dendrimeric structure and Multiple Antigen Peptide (MAP) forms, particularly in the form of Compound A below, and discloses the ability of M33 to neutralise LPS. In the 4 antibacterial peptide sequences of WO2010038220 listed above, all amino acids are in the L-configuration.

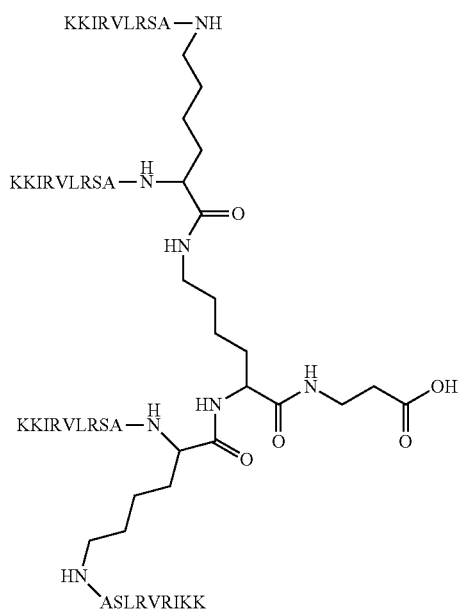

Compound A

WO2012010266 discloses that when the L-amino acids of M33 and its functional analogues are substituted with their relative D-amino acid counterpart, the resulting peptides still possess antibacterial activity.

M33-derived tetrabranched peptides, wherein M33 is in either an all-L or in an all-D configuration, are known from Falciani et al. (2012) to bind both LTA and LPS in an assay whereby their biotinylated derivative is immobilized on streptavidin-coated cells (i.e. non covalently attached to a solid support).

EP1789436 discloses MPA peptides having similar, but not identical, sequences to the M33 peptide and the M33 functional analogues of this invention, their synthesis via solid-phase synthesis (where the peptides, when bound to a solid support are fully side-chained protected) and their activity against LPS in a biacore assay (where the moiety bound to the solid support is LPS, but not the antimicrobial peptide).

Gustafsson et al. (2010) $_{[41]}$disclose various antimicrobial peptides and their LPS-binding activity when immobilized on solid support. Similarly, Costa et al. (2011) discloses how antimicrobial peptides can be covalently attached onto solid support.

DETAILED DESCRIPTION OF THE INVENTION

Figure 1:
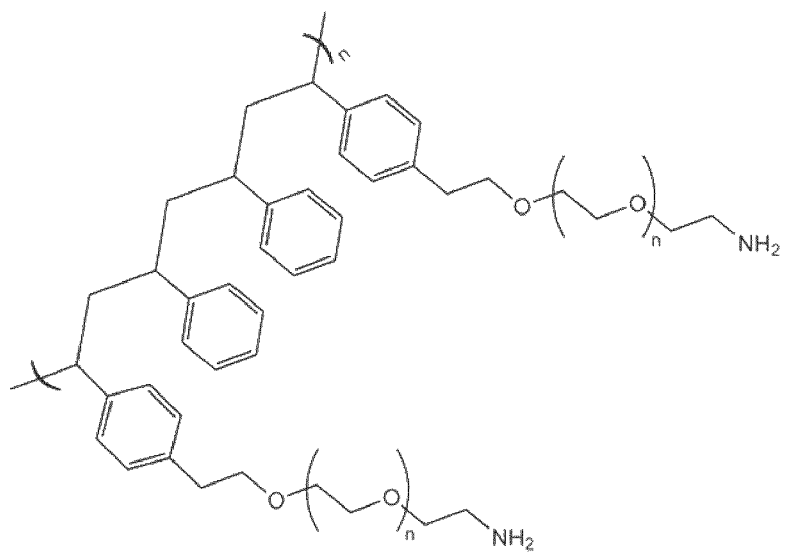
FIG. 1. depicts a composite resin of crosslinked hydroxyethylpolystyrene and polyethylene glycol.

We have surprisingly determined that when M33 is covalently bound through its C-terminus to a solid support, particularly when bound to such structure by the formation of a covalent bond with either compound A or compound B below, it allows for the selective removal of LPS from the biological fluid without altering the protein content of the fluid.

Such derivatized solid support can also be used to remove LTA from the biological fluid.

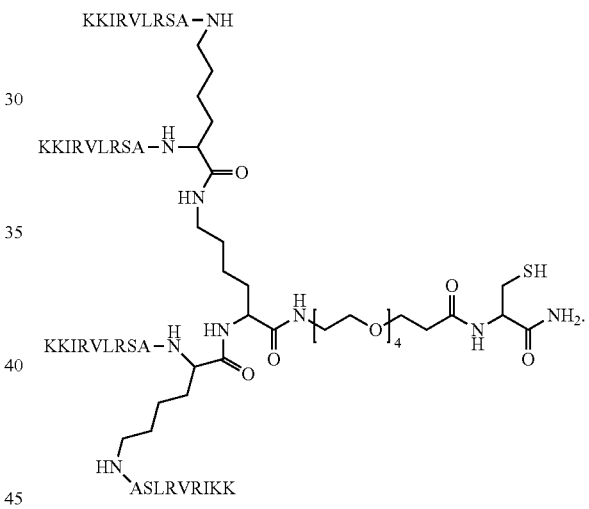

Compound B

Accordingly, in a first aspect of this invention, there is provided a method for the removal of a bacterial toxin selected from the list of LPS and LTA from a biological fluid, said method comprising contacting the biological fluid with a peptide selected from the list of KKIRVRLSA (SEQ ID NO:1), RRIRVRLSA (SEQ ID NO:2), KRIRVRLSA (SEQ ID NO: 3) and RKIRVRLSA (SEQ ID NO:4), which peptide is covalently attached to a solid support through its C-terminus, optionally with the interposition of a linker, and wherein all amino acids of the peptide are either in the L- or the D-configuration.

In one embodiment, all amino acids of the peptide selected from the list of KKIRVRLSA (SEQ ID NO:1), RRIRVRLSA (SEQ ID NO:2), KRIRVRLSA (SEQ ID NO: 3) and RKIRVRLSA (SEQ ID NO:4), are in the L-configuration.

In another embodiment, all amino acids of the peptide selected from the list of KKIRVRLSA (SEQ ID NO:1), RRIRVRLSA (SEQ ID NO:2), KRIRVRLSA (SEQ ID NO: 3) and RKIRVRLSA (SEQ ID NO:4), are in the D-configuration.

In one embodiment, the peptide-linker moiety is a radical of the formula below

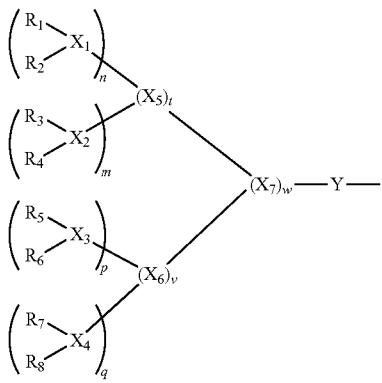

wherein $R_1$—, $R_2$—, $R_3$—, $R_4$—, $R_5$—, $R_6$—, $R_7$— and $R_8$— can be the same or different and are selected from KKIRVRLSA—(SEQ ID NO:1), RRIRVRLSA—(SEQ ID NO:2), KRIRVRLSA—(SEQ ID NO: 3) and RKIRVRLSA—(SEQ ID NO:4);

$X_1$, $X_2$, $X_3$, $X_4$, $X_5$, $X_6$ and $X_7$ are the same or different and are an at least bifunctional residue;

n, m, p, q, t, v and w can be the same or different and can be nil or 1, and at least one of m, n, p and q is 1, with the proviso that if t is nil, then n and m are nil and at least one of p and q are 1, that if v is nil then p and q are nil and at least one of m and n are 1 and that if w is nil then v is nil and at least one of m and n are 1;

Y is a bond or a spacer.

In one embodiment, $X_1$, $X_2$, $X_3$, $X_4$, $X_5$, $X_6$ and $X_7$ are the same or different and each comprise at least two functional amino groups.

In another embodiment, $X_1$, $X_2$, $X_3$, $X_4$, $X_5$, $X_6$ and $X_7$ are the same or different and are selected from a lysine residue, an ornithine residue, a norlysine residue, an amino alanine residue and a diaminopropionic acid residue.

In one embodiment, at least one of $R_1$—, $R_2$—, $R_3$—$R_4$—, $R_5$—, $R_6$—, $R_7$— and $R_8$— is KKIRVRLSA—(SEQ ID NO:1).

In another embodiment, each of $R_1$—, $R_2$—, $R_3$—$R_4$—, $R_5$—, $R_6$—, $R_7$— and $R_8$— is KKIRVRLSA—(SEQ ID NO:1).

In one embodiment, Y is selected from the list of an amino acid residue and a peptide.

In a particular embodiment, Y is selected from the list of an amino acid residue, a dipeptide, a tripeptide, a tetrapeptide, a pentapeptide, an hexapeptide, an octapeptide, a nonapeptide and a decapeptide.

In a more particular embodiment, Y is selected from the list of a beta-alanine residue, an N-(PEG)$_y$-CH$_2$—CH$_2$—C(O) residue wherein 1≤y≤11, a cysteine residue and a peptide comprising such residue.

In an even more particular embodiment, the peptide of the previous embodiment is selected from the list of, a dipeptide, a tripeptide, a tetrapeptide, a pentapeptide, an hexapeptide, an octapeptide, a nonapeptide, a decapeptide.

In one embodiment y is selected from the list of 1, 2, 3, 4, 5, 6, 7, 8, 9, 10 and 11.

In one embodiment w is nil, v is nil, t is 1, m is 1 and n is 1.

In a particular embodiment w is nil, v is nil, t is 1, m is 1, n is 1 and $X_1$, $X_2$ and $X_5$ each are a lysine residue.

In a particular embodiment, w is nil, v is nil, t is 1, m is 1 and n is 1 and at least one of $R_1$—, $R_2$—, $R_3$— and $R_4$—, is KKIRVRLSA—(SEQ ID NO:1).

In a particular embodiment, w is nil, v is nil, t is 1, m is 1 and n is 1 and each of $R_1$—, $R_2$—, $R_3$— and $R_4$—, is KKIRVRLSA—(SEQ ID NO:1).

In some embodiments, the solid support is porous.

In one embodiment, the solid support is a crosslinked agarose resin.

In another embodiment, the solid support is a composite resin of crosslinked hydroxyethylpolystyrene and polyethylene glycol.

In some embodiments, the biological fluid is selected from the list of serum, plasma and blood.

All embodiments of this first aspect of the invention may be combined.

In a second aspect of this invention, there is provided a solid support carrying the radicals as above described in the embodiments of the first aspect of this invention.

In a third aspect of this invention, there is provided an item selected from the list of a column and a cartridge, each of which comprises the solid support of the second aspect of this invention.

In a fourth aspect of this invention, there is provided a medical apparatus comprising the solid support of the second aspect of this invention or the item of the third aspect of this invention.

In a particular embodiment, the medical apparatus is a medical apparatus for the removal of a bacterial toxin selected from the list of LPS and LTA from biological fluids.

In a fifth aspect of this invention, there is provided the use of the medical apparatus of the fourth aspect of this invention for the removal of a bacterial toxin selected from the list of LPS and LTA from biological fluids.

EXAMPLES

The invention is now described by means of non-limiting examples.

Example 1: Synthesis of Resin-Bound Compound A

Compound A was synthesized on 100 mg NovaSyn TG resin (0.24 mmol/g) (Novabiochem).

This resin a is a composite of low cross-linked hydroxyethylpolystyrene and 3000-4000 MW polyethylene glycol, which has been terminally functionalized with amino groups. (FIG. 1)

Peptide synthesis was carried out on an automated synthesizer Syro (MultiSynTech, Witten, Germany) using 9-fluorenylmethoxycarbonyl (Fmoc) chemistry and O-(benzotriazol-1-yl)-N,N,N,N-tetramethyluronium hexafluorophosphate (HBTU)/1,3-isopropylethylamine (DIPEA) activation. Side-chain-protecting groups were tert-butoxycarbonyl for Lys, 2,2,4,6,7-pentamethyldihydrobenzofuran-5-sulfonyl for Arg, and tert-butyl ether for Ser. The first amino acid was Fmoc-βAla-OH.

Two consecutive coupling steps with Fmoc-Lys(Fmoc)-OH were used to build the lysine core, followed by sequential addition of Fmoc amino acids to complete the peptide KKIRVRLSA (SEQ ID NO:1). Finally Compound A on resin was side-chain deprotected by treatment with trifluoroacetic acid containing water and triisopropylsilane (95:2.5:2.5). The peptidyl-resin was then washed four times with DCM, four times with MeOH, three times with acetic acid 1M, four times with H2O and four times with MeOH.

Example 2: Synthesis of Compound B

Compound B was produced by solid-phase synthesis through standard Fmoc chemistry with a Syro multiple peptide synthesizer (MultiSynTech, Witten, Germany). The peptide was synthesized on TentaGel S RAM resin with Fmoc —NH-Cys(Trt)-COOH as first amino acid in C-terminus, Fmoc-NH-PEG(4)-CH$_2$—CH$_2$—COOH was added in second coupling step, then Fmoc-Lys(Fmoc)-OH was added twice to build the tetrameric core. Followed by the nine sequential additions of Fmoc amino acids to complete the peptide KKIRVRLSA. Side chain protecting groups were 2,2,4,6,7-pentamethyldihydrobenzofuran-5-sulfonyl for R, t-butoxycarbonyl for K and t-butyl for S. The final product was cleaved from the solid support and deprotected by treatment with TFA containing triisopropylsilane, water (95/2.5/2.5), and precipitated with diethyl ether. Crude peptides were purified by reversed-phase chromatography on a preparative column (XBridge peptide BEH C18 Waters), in linear gradient for 40 min, from 75% to 65% A, where A is 0.1% TFA/water and B is acetonitrile (rt=22 min). Final peptide purity and identity was confirmed by reversed phase chromatography on a Phenomenex Jupiter C18 analytical column (300 A°, 5 µm, 250×4.6 mm) with the same gradient as above and by mass spectrometry MALDI TOF/TOF (Ultraflex III Bruker Daltonics) (M$^+$: found 7723, 5; calculated 7724, 1).

Example 3: Synthesis of Resin-Bound Compound B

Figure 2:
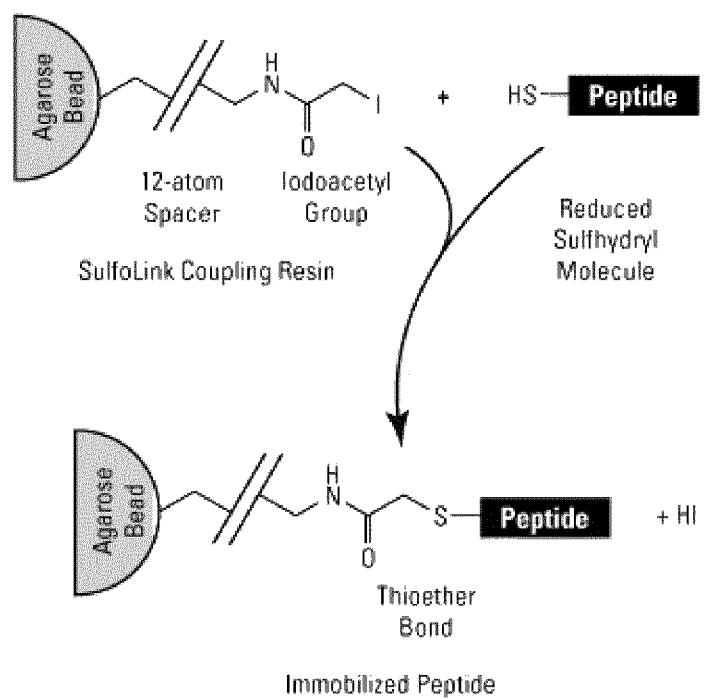
FIG. 2. depicts how a covalent bond is formed between the Sulfolink™ resin and a free thiol.

Compound B was attached via its sulfhydryl to a Sulfolink™ resin, which is a cross linked agarose resin, as depicted in FIG. 2.

Compound B (1 mg/ml) diluted in 4 ml was resuspended and incubated for 30 minutes at room temperature in Coupling Buffer (50 mM Tris, 5 mM EDTA-Na; pH 8.5).

The SulfoLink™ Resin (SulfoLink® Immobilization Kit for Peptides, Pierce Biotechnology, Rockford, Ill., USA) in its cartridge/column (5 ml column, 1 cm diameter, volume of the resin 2 ml) was resuspended by mixing, and the storage buffer was removed by centrifuging at 1,000×g for 1 minute positioning the column in a 15 ml collection tube. 2 ml of Coupling Buffer (as above) was added on the resin, then the mix was centrifuged and this step was repeated once. 2 ml of the compound B solution was added and mixed by rocking or end-over-end mixing at room temperature for 15 minute. Then, the column was positioned upright and incubated at room temperature for 30 minutes without mixing. The step was repeated twice.

Figure 3:
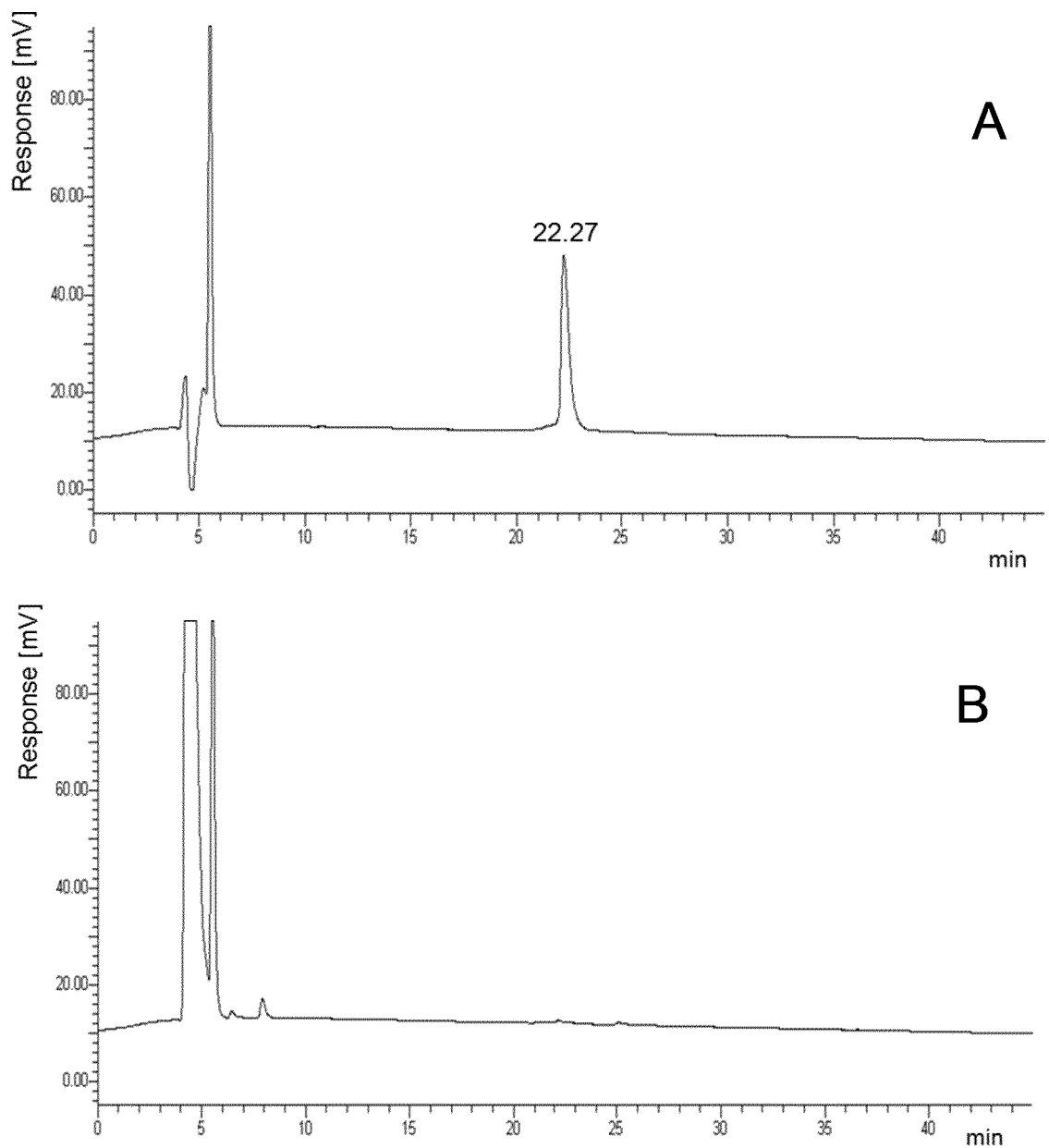
FIG. 3. depicts the HPLC profiles of a solution containing compound B before (A) and after (B) coupling to a Sulfolink™ resin.

The column was placed into a new 15 ml collection tube and centrifuged to collect non-bound peptide. The flow-through was saved in order to determine the coupling efficiency by HPLC As set out in FIG. 3, where compound B elutes at 22.27 minutes, the coupling efficiency was optimal.

The column was washed and centrifuged for three times. Then, the column was washed with Coupling Buffer 2 ml and centrifuged. 50 mM cysteine in Coupling Buffer was then applied to the column and mixed for 45 minutes at room temperature, in order to block unreacted binding sites. After further centrifugation, the column was allowed to drain.

Example 4: Resin-Bound Compound B Removes LPS from a Biological Fluid and does not Significantly Alter the Serum Protein Content 2 ml of compound B-loaded resin of example 3, in its 5 ml column (5 ml column, diameter 1 cm, volume of the resin 2 ml) were used. 2 ml of human serum containing LPS from *E. coli* O111:B4 (Sigma, St. Louis, Mo.) (5 ng/ml) were incubated with the resin into the cartridge for 2 hours at room temperature under constant rocking. Then the sample was collected and measured for the LPS amount by the Limulus Amebocyte Lysate (LAL) test as described in material and methods.

As a negative control, the same amount of resin not loaded with compound B was incubated with the same amount of serum and its LPS content determined as above.

As another control, the LPS content of an untreated serum aliquot was also measured.

Figure 4:
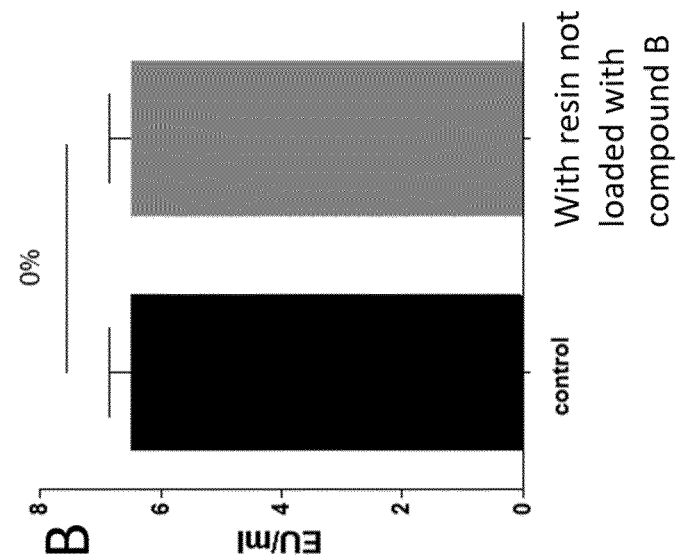
FIG. 4 depicts the LPS content of a biological fluid before and after having been exposed to a resin derivatized with compound B (A) and to the same, underivatized, resin (B).
Figure 4:
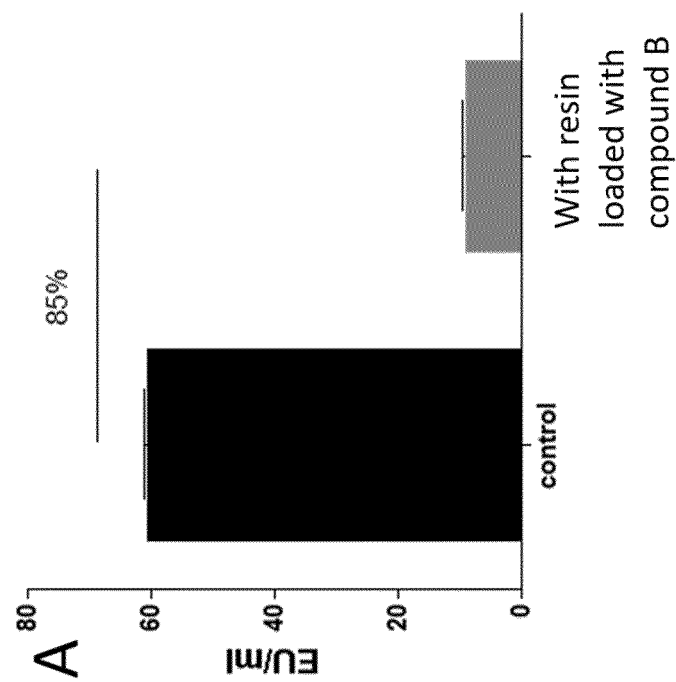

As set out in FIG. 4, the loaded resin was able to remove 85% of *E. coli* LPS from serum, whereas the unloaded resin did not remove LPS at all.

Figure 6:
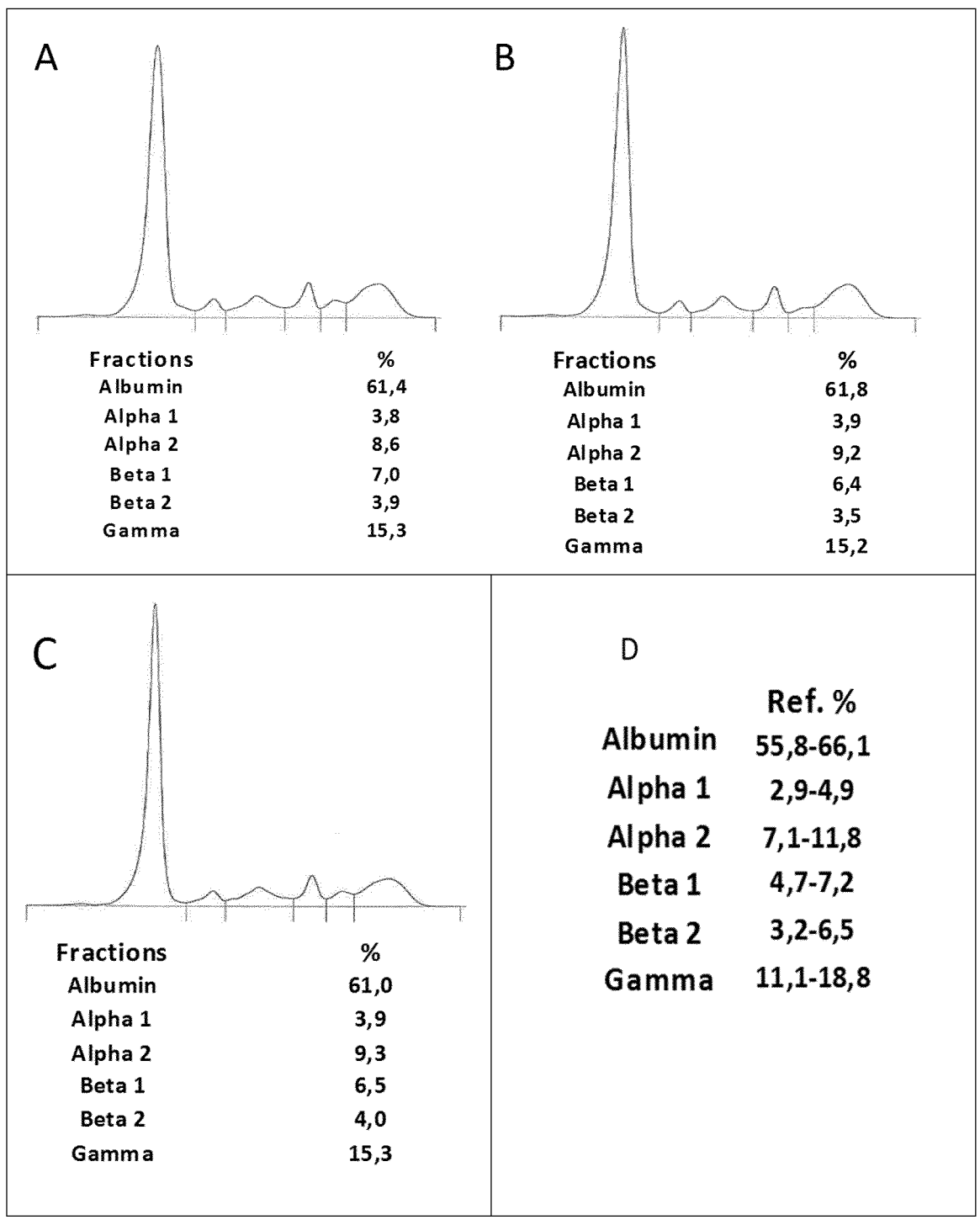
FIG. 6 depicts the protein electrophoresis profiles of a serum sample (A), a serum sample after having been in contact with a resin derivatised with compound B (B), a serum sample after having been in contact with a resin derivatised with compound A (C), and the references values for such proteins (D).

As set out in FIGS. 6A and 6B, which respectively depict the capillary electrophoresis profiles of sera before and after passage onto the compound B-loaded resin such passage does not significantly alter the serum protein content.

Figure 5:
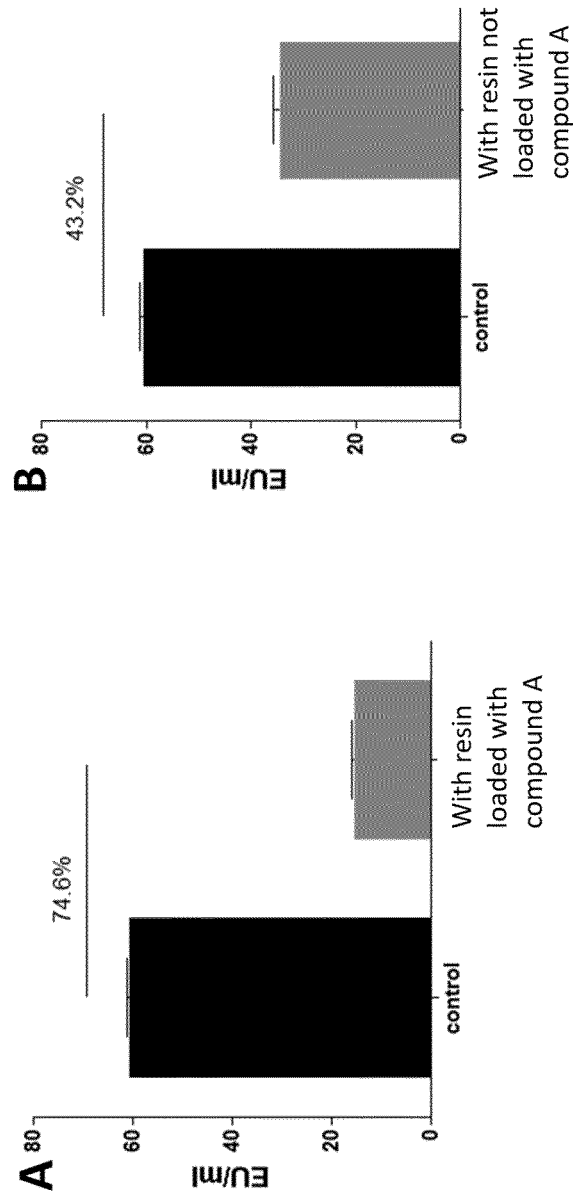
FIG. 5 depicts the LPS content of a biological fluid before and after having been exposed to a resin derivatised with compound B A (A) and the same, underivatized, resin (B).

Example 5: Resin-Bound Compound a Removes LPS from a Biological Fluid and does not Significantly Alter the Serum Protein Content 1 ml of the compound A-loaded resin of example 1 were loaded into a 5 ml column (5 ml column, diameter 1 cm. Using the same procedure described in example 4, it was determined, as set out in FIG. 5, the compound A-loaded resin was able to remove more than 74% LPS from *E. coli*, whereas the unloaded resin removed 43% of LPS.

As set out in FIGS. 6A and 6C, which respectively depict the capillary electrophoresis profiles of sera before and after passage onto the compound A-loaded resin, such passage does not significantly alter the serum protein content.

Example 6: Resin-Bound Compound B Removes LTA from Phosphate Buffered Saline Solution Containing LTA 2 ml of compound B-loaded resin of example 3, in its 5 ml column (5 ml column, diameter 1 cm, volume of the resin 2 ml) were used. 1 ml of phosphate buffered saline (PBS) solution containing LTA from *S. aureus* (MyBiosource, San Diego, Calif., US) (500 pg/ml) were incubated with the resin into the cartridge for 2 hours at room temperature under constant rocking. Then the sample was collected and measured for the LTA amount by the Human LTA (lipoteichoic acids) ELISA Kit as described in material and methods.

Figure 7:
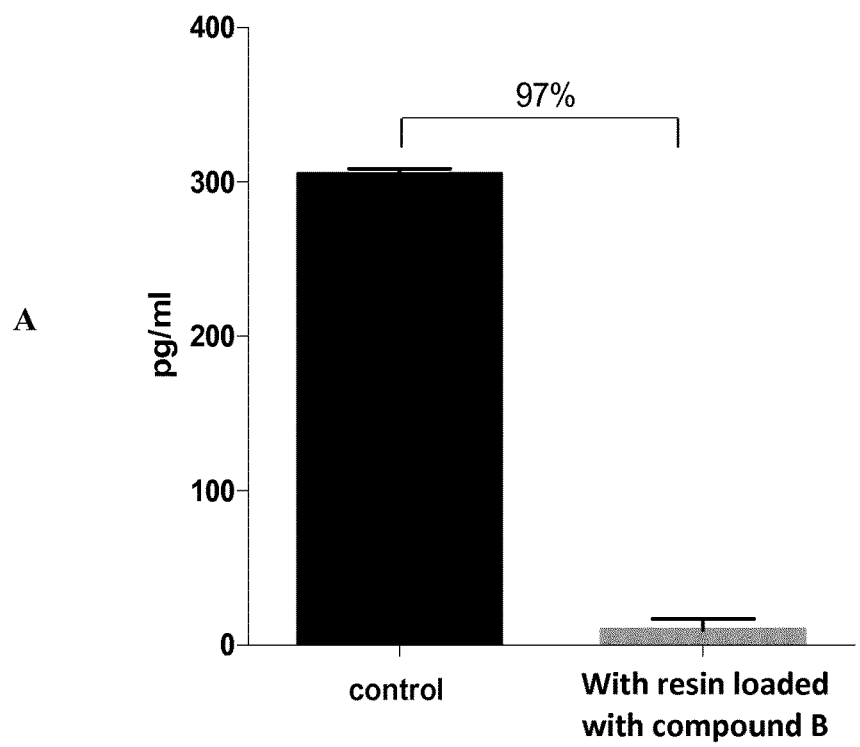
FIG. 7 depicts the LTA content of a biological fluid before and after having been exposed to a resin derivatised with compound B (A) and the same, underivatized, resin (B).
Figure 7:
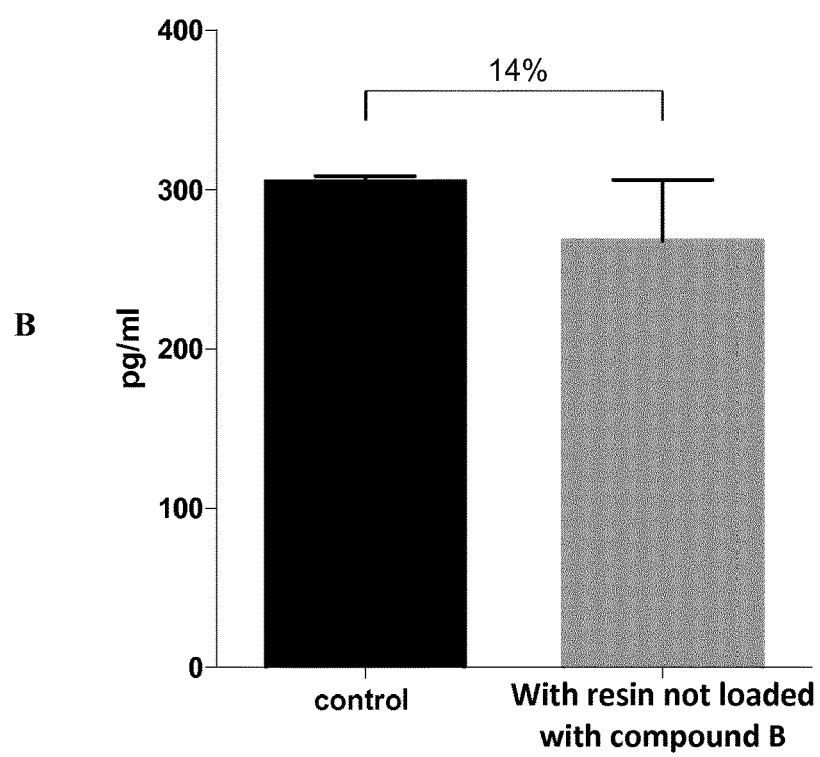

As a negative control, the same amount of resin not loaded with compound B was incubated with the same amount of PBS and its LTA content determined as above. As set out in FIG. 7, the loaded resin was able to remove 97%% of LTA from *S. aureus*, whereas the unloaded resin only removed 14%.

Materials & Methods

Measurement of LPS by LAL Test

Analysis of LPS removal was performed using the LAL Chromogenic Endotoxin Quantitation Kit (ThermoFisher Scientific, Waltham, US), which is an indicator of the presence of free LPS.

A standard curve (0.1-1 EU/ml) was prepared using a control standard endotoxin from *Escherichia coli* (O111:B4) in endotoxin-free water, and serially diluted. Serum samples were diluted 50 and 100 fold in endotoxin-free water. Each sample was processed in duplicate.

The microplate was equilibrated in a heating block for 10 minutes at 37° C. Then, 50 μL of each standard and sample were dispensed into a microplate well and incubated for 5 minutes at 37° C.

50 μL of Limulus Amebocyte Lysate (LAL) was added to each well and the plate was incubated for 10 minutes at 37° C. After exactly 10 minutes, 100 μL of Chromogenic Substrate solution was added to each well. The plate was incubated for 6 minutes at 37° C. In the end, 50 μL of Stop Reagent (25% acetic acid) was added. The absorbance at 405-410 nm was measured on a plate reader (Ascent Software). EUs were calculated on the base of standard curve obtained as described above.

Measurement of LTA by ELISA

The LTA content of a sample can be readily determined by the use of commercial kits to that effect. One example of such kits is the Antibody Research Corporation (St. Charles, Mo.) LTA ELISA kit. The sample is added to micro-plate wells pre-coated with Lipoteichoic acids antibody. After incubation and washing, a lipoteichoic acids detection antibody labeled with biotin is added. After appropriate incubation, a streptavidin-horse radish peroxidase (HRP) conjugate is added followed by incubation and washing to remove the uncomplexed enzymes. After addition of a chromogenic 3,3',5,5'-tetramethylbenzidine (TMB) solution the sample is incubated for 5 minutes. The HRP enzyme reaction is stopped by addition of a sulphuric acid solution. The intensity of color developed is proportional to the concentration of the Lipoteichoic acids present in the sample and read at 450 nM using a plate reader. Concentration of Lipoteichoic acid in the sample is determined by interpolating the absorbance value in the standard curve.

Analysis of LTA removal was performed using Human LTA (lipoteichoic acids) ELISA Kit (MyBiosource, San Diego, Calif., US).

A standard curve (7.8-500 pg/ml) was prepared using a control standard lipoteichoic acid from *S. aureus* in Sample/Standard dilution buffer, and serially diluted.

Samples were diluted 2 and 10 fold in Sample/Standard dilution buffer. Each sample was processed in duplicate.

The microplate was washed two times before adding standard, sample and control (zero) wells. Then 100 μL of each standard and sample were dispensed into a microplate well and incubated for 90 minutes at 37° C.

100 μL of Biotin-detection Antibody working solution was added into the above wells and incubated for 60 minutes at 37° C.

The plate was washed three times with Wash Buffer.

100 μL of HRP-Streptavidin conjugate (SABC) working solution was added to each well and the plate was incubated for 30 minutes at 37° C. After exactly 30 minutes, the plate was washed five times with Wash Buffer.

90 μL of TMB substrate solution was added to each well. The plate was incubated for 15-30 minutes at 37° C. in dark. In the end, 50 μL of Stop Solution was added. The absorbance at 450 nm was measured on a plate reader (Ascent Software). The LTA concentration was calculated on the base of standard curve obtained as described above.

Capillary Electrophoresis

Human serum was analyzed before and after the passage into compound A or B-loaded resins by capillary electrophoresis by the clinical device Capillarys (4.51 software; Sebia) following producer instructions. The instrument provided amount of protein present in the samples in g/L, also showing the profile of electrophoretic curves with relative content in percentage, calculated on the area beyond the curve.

REFERENCES

Ala-Kokko T I, Laurila J, Koskenkari J, A new endotoxin adsorber in septic shock: observational case series. Blood Purif. 2011, 34:303-9

Cohen J, Aslam M, Pusey C D, Ryan C J, Protection from endotoxemia: a rat model of plasmapheresis and specific adsorption with polymyxin B. J Infect Dis, 1987, 155(4): 690-5

Costa F, Carvalho I F, Montelaro R C, Gomes P, Martins M C L, Acta Biomaterialia, 7 (2011), 1431-1440

Falciani, C., Lozzi, L., Pollini, S., Luca, V., Carnicelli, V., Brunetti, J., Lelli, B., Bindi, S., Scali, S., Di Giulio, A., Rossolini, G. M., Mangoni, M. L., Bracci, L., *Pini*, A. (2012) Isomerization of an antimicrobial peptide broadens antimicrobial spectrum to gram-positive bacterial pathogens. PLoS One, 2012, 7, e46259.

Gustafsson A, Olin A I, Ljunggren L, Scandinavian Journal of Clinical and Laboratory Investigation, 2010, 70: 194-200

Hotchkiss R S, Moldawer L L, Opal S M, Reinhart K, Turnbull I R, Vincent J L. Sepsis and septic shock. Nat Rev Dis Primers. 2016, 2:16045

Ianaro A, Tersigni M, D'Acquisto F. New insight in LPS antagonist. Mini Rev Med Chem. 2009 9:306-17

Kang S S, Sim J R, Yun C H, Han S H. Lipoteichoic acids as a major virulence factor causing inflammatory responses via Toll-like receptor 2. Arch Pharm Res. 2016, 39:1519-1529

Lakshmikanth C L, Jacob S P, Chaithra V H, de Castro-Faria-Neto H C, Marathe G K. Sepsis: in search of cure. Inflamm Res. 2016, 65:587-602

Perner A, Rhodes A, Venkatesh B, Angus D C, Martin-Loeches I, Preiser J C, Vincent J L, Marshall J, Reinhart K, Joannidis M, Opal S M. Sepsis: frontiers in supportive care, organisation and research. Intensive Care Med. 2017, 43:496-508

Rocco and Klein, Polymyxin B hemoperfusion: a mechanistic perspective. Critical care, 2014, 18:309

Roscia, G., Falciani, C., Bracci, L., Pini, A. The development of antimicrobial peptides as new antibacterial drugs. Curr Protein Pept Sci. 2013, 14: 641-649

Shoji H, Tani T, Hanasawa K, Kodama M. Extracorporeal endotoxin removal by polymyxin B immobilized fiber cartridge: designing and antiendotoxin efficacy in the clinical application. Therapeutic Apheresis, 1998, 2:3-12

The invention claimed is:

1. A method for removing bacterial toxins selected from the list of lipopolysaccharide (LPS) and lipoteichoic acid (LTA) from a biological fluid, said method comprising contacting the biological fluid with a peptide selected from the list of KKIRVRLSA (SEQ ID NO:1), RRIRVRLSA (SEQ ID NO:2), KRIRVRLSA (SEQ ID NO:3) and RKIRVRLSA (SEQ ID NO:4) which is covalently attached to a solid support through its C-terminus, optionally with the interposition of a linker, whereby a linker-peptide moiety is formed and wherein all amino acids of the peptide are either in the L- or the D-configuration, and wherein the peptide-linker moiety is a radical of the formula $$\left(\begin{array}{c}R_1\\R_2\end{array}\!\!\!\diagdown\!\! X_1\right)_n \left(\begin{array}{c}R_3\\R_4\end{array}\!\!\!\diagdown\!\! X_2\right)_m \left(\begin{array}{c}R_5\\R_6\end{array}\!\!\!\diagdown\!\! X_3\right)_p \left(\begin{array}{c}R_7\\R_8\end{array}\!\!\!\diagdown\!\! X_4\right)_q \begin{array}{c}(X_5)_t\\ \\(X_6)_v\end{array}\!\!\!\!(X_7)_w\!\!-\!\!Y\!-\!\!$$

wherein $R_1$—, $R_2$—, $R_3$—, $R_4$—, $R_5$—, $R_6$—, $R_7$— and $R_8$— can be the same or different and are selected from KKIRVRLSA—(SEQ ID NO:1), RRIRVRLSA—(SEQ ID NO:2), KRIRVRLSA—(SEQ ID NO:3) and RKIRVRLSA—(SEQ ID NO:4); $X_1$, $X_2$, $X_3$, $X_4$, $X_5$, $X_6$ and $X_7$ are the same or different and are an at least bifunctional residue;

n, m, p, q, t, v and w can be the same or different and can be nil or 1, and at least one of m, n, p and q is 1, with the proviso that if t is nil, then n and m are nil and at least one of p and q are 1, if v is nil then p and q are nil and at least one of m and n are 1, if w is nil then v is nil and at least one of m and n are 1; and Y is a bond or a spacer.

2. The method of claim 1, wherein $X_1$, $X_2$, $X_3$, $X_4$, $X_5$, $X_6$ and $X_7$ are the same or different and each comprise at least two functional amino groups.

3. The method of claim 2, wherein $X_1$, $X_2$, $X_3$, $X_4$, $X_5$, $X_6$ and $X_7$ are the same or different and are selected from a lysine residue, an ornithine residue, a norlysine residue, an amino alanine residue and a diaminopropionic acid residue.

4. The method of claim 1, wherein at least one of $R_1$—, $R_2$—, $R_3$—$R_4$—, $R_5$—, $R_6$—, $R_7$— and $R_8$— is KKIRVRLSA—(SEQ ID NO:1).

5. The method of claim 1, wherein Y is an amino acid residue or a peptide.

6. The method of claim 5, wherein Y is selected from the list of a beta-alanine residue, an N-(PEG)$_y$-CH2-CH2-C(O)— residue wherein $1 \leq y \leq 11$, a cysteine residue and a peptide comprising such residues.

7. The method of claim 1, wherein w is nil, v is nil, t is 1, m is 1 and n is 1.

8. The method of claim 7, wherein $X_1$, $X_2$ and $X_5$ each are a lysine residue.

9. The method of claim 7 wherein at least one of $R_1$—, $R_2$—, $R_3$— and $R_4$— is KKIRVRLSA—(SEQ ID NO:1).

10. The method of claim 1, wherein the solid support is selected from the list of a crosslinked agarose resin and a composite resin of crosslinked hydroxyethylpolystyrene and polyethylene glycol.

\* \* \* \* \*

SEQUENCE LISTING

<160> NUMBER OF SEQ ID NOS: 4

<210> SEQ ID NO 1
<211> LENGTH: 9
<212> TYPE: PRT
<213> ORGANISM: Artificial Sequence
<220> FEATURE:
<223> OTHER INFORMATION: synthetic peptide

<400> SEQUENCE: 1

Lys Lys Ile Arg Val Arg Leu Ser Ala
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic peptide

<400> SEQUENCE: 2

Arg Arg Ile Arg Val Arg Leu Ser Ala
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic peptide

<400> SEQUENCE: 3

Lys Arg Ile Arg Val Arg Leu Ser Ala
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic peptide

<400> SEQUENCE: 4

Arg Lys Ile Arg Val Arg Leu Ser Ala
1               5